United States Patent

Cianci et al.

[11] Patent Number: 5,167,623
[45] Date of Patent: Dec. 1, 1992

[54] MULTILUMEN CATHETER

[75] Inventors: James P. Cianci, Walpole; James R. Gross, Wareham, both of Mass.; David C. Beattie, Salt Lake City, Utah; Troy Nichols, Baltimore, Md.

[73] Assignee: The Kendall Company, Mansfield, Mass.

[21] Appl. No.: 634,640

[22] Filed: Dec. 27, 1990

[51] Int. Cl.⁵ .............................................. A61M 3/00
[52] U.S. Cl. ...................................... 604/43; 604/280
[58] Field of Search ............... 604/27, 39, 43, 93, 604/158, 264, 280, 283, 284, 164

[56] References Cited

U.S. PATENT DOCUMENTS

| | | |
|---|---|---|
| 1,211,928 | 1/1917 | Fisher . |
| 3,087,493 | 4/1963 | Schossow .............................. 128/351 |
| 3,548,805 | 12/1970 | Datsenko et al. ..................... 128/2 |
| 3,593,713 | 7/1971 | Bogoff .................................. 604/280 |
| 3,929,126 | 12/1975 | Corsaut ................................ 128/240 |
| 4,714,460 | 12/1987 | Calderon .............................. 604/43 |
| 4,721,115 | 1/1988 | Owens ................................. 128/713 |
| 4,722,344 | 2/1988 | Cambron et al. ..................... 604/280 |
| 4,811,737 | 3/1989 | Rydell .................................. 128/344 |
| 4,867,742 | 10/1989 | Calderon .............................. 604/43 |
| 4,958,634 | 9/1990 | Jang .................................... 606/194 |
| 4,966,583 | 10/1990 | Debbas ................................. 604/98 |
| 4,981,482 | 1/1991 | Ichikawa .............................. 606/108 |
| 4,994,033 | 2/1991 | Shockey et al. ...................... 604/101 |
| 5,059,170 | 10/1991 | Cameron .............................. 604/43 |
| 5,078,681 | 1/1992 | Kawashima .......................... 604/53 |
| 5,108,369 | 4/1992 | Ganguly et al. ...................... 604/102 |

FOREIGN PATENT DOCUMENTS 2565491 12/1985 France .............................. 604/284

Primary Examiner—John D. Yasko
Assistant Examiner—Anthony Gutowski
Attorney, Agent, or Firm—Alvin Isaacs

[57] ABSTRACT

A multilumen catheter having a distal portion with a soft tip and reduced cross-section. The multilumen catheter of the present invention includes a flexible, elongated first catheter tube and a flexible, elongated, dual-lumen catheter tube which has a first and second lumens integrally formed and is disposed within the first catheter tube. The cross-section of the dual-lumen catheter tube is smaller than that of the first catheter tube and therefore, an independent, single lumen is defined in the space between the first catheter tube and the dual-lumen catheter tube. The dual-lumen catheter tube extends beyond the distal end of the first catheter tube thereby providing an overall reduced cross-section of the distal portion of the present multilumen catheter. Furthermore, the dual-lumen catheter tube may be formed from a softer material than that of the first cathether tube thereby providing a softer distal portion of the present multilumen catheter. A protective hub encapsulates and secures the proximal ends of the first and dual-lumen catheter tubes, and facilitates fluid communication between each of the lumens and fluid transfer devices.

13 Claims, 3 Drawing Sheets

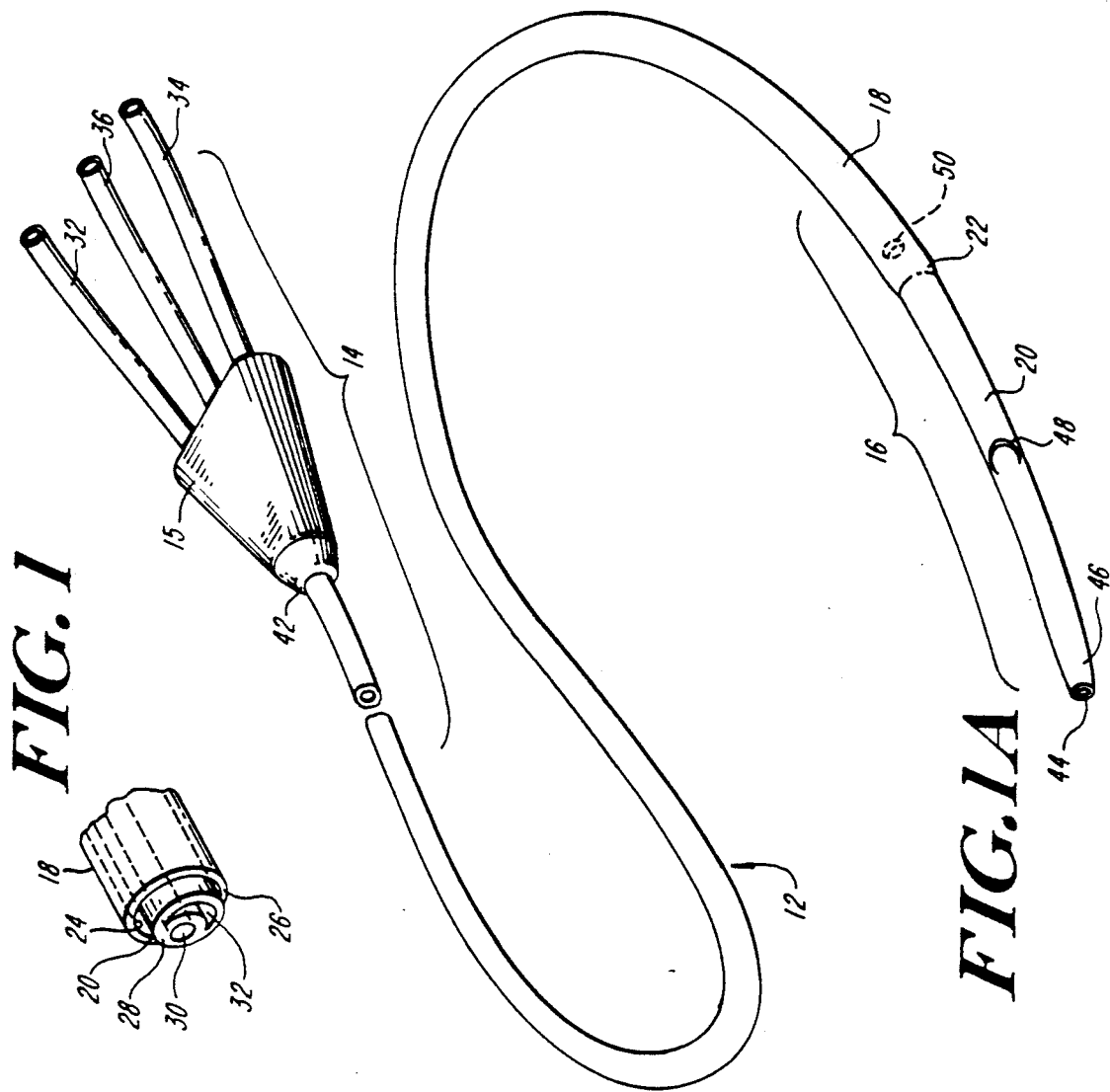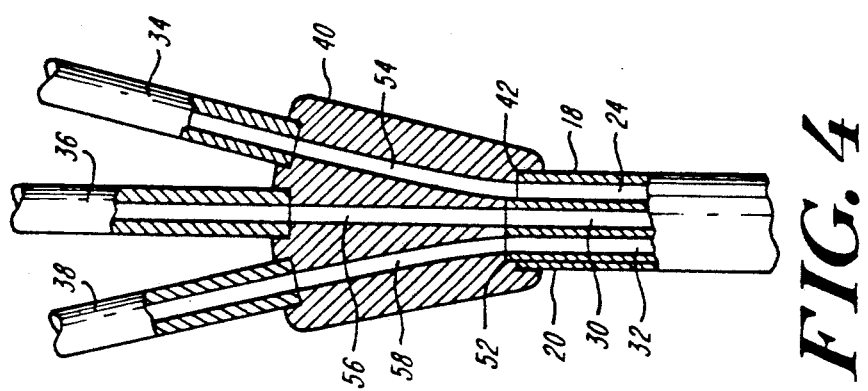

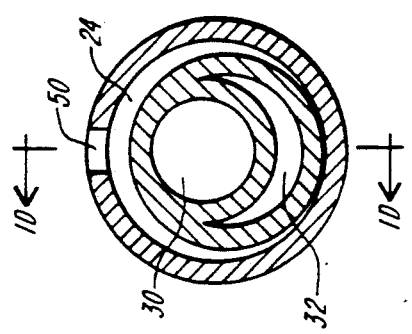
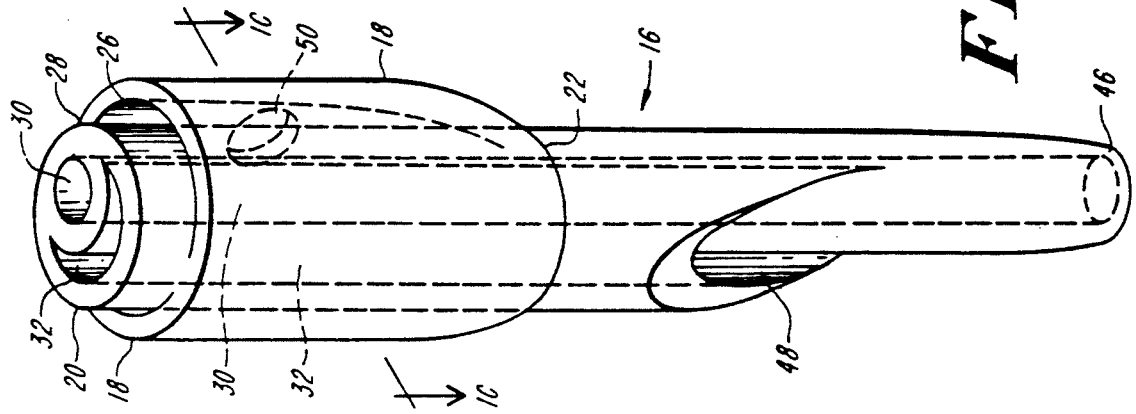
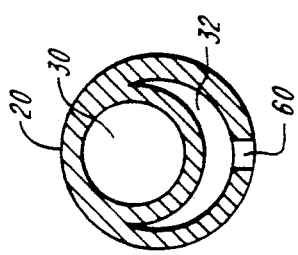
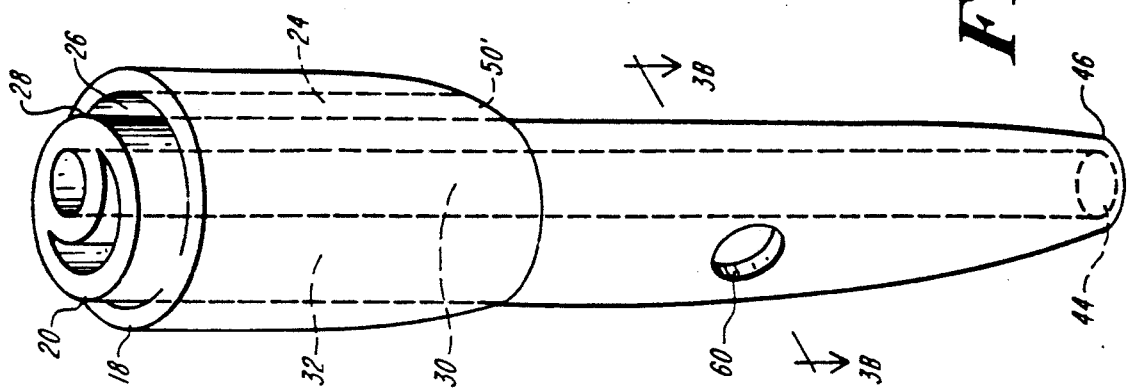

MULTILUMEN CATHETER

FIELD OF THE INVENTION

This invention relates to catheters, and more particularly to multilumen catheters.

BACKGROUND OF THE INVENTION

Conventional multilumen catheters are used to simultaneously infuse a plurality of fluids into a patient. The separate lumens of the catheters prevent fluids from interacting during the infusion process and before the fluids enter the patient's body. Maintaining fluids separately is particularly critical when the fluids to be simultaneously infused are chemically incompatible.

Furthermore, multilumen catheters may be used to infuse fluids such as medication into a patient's body while simultaneously withdrawing samples such as blood from the patient thereby eliminating the need for separate means of infusing and withdrawing fluids from a patient and minimizing patient discomfort.

Furthermore, conventional multilumen catheters cannot be easily inserted without the use of a dilator due to the cross-sectional size of the distal end of the catheter. The use of a dilator creates an extra step on the part of the surgeon or other health care personnel inserting the catheter. The extra time needed to insert and remove a dilator prior to the insertion of the catheter is extremely undesirable in emergency situations. Furthermore, the insertion of a dilator prior to catheter insertion may cause the patient to bleed more profusely as well as subjecting the patient to possible increased discomfort.

Therefore, it is desirable to have a multilumen catheter which may be quickly and easily inserted without the above described disadvantages, and which is economical to produce and compatible with existing medical equipment used with multiple lumen catheters.

SUMMARY OF THE INVENTION

The multilumen catheter of the present invention comprises a first elongated flexible catheter tube having a proximal end, a distal end and an outer wall and an inner wall. An elongated, flexible dual-lumen catheter tube having a proximal end, a distal end, an outer wall, and a cross-section which is smaller than that of the first catheter tube, is disposed within the first catheter tube, abutting a portion of the proximal inner wall of the first catheter tube, and defining a single lumen between the inner wall of the first catheter tube and the outer wall of the second catheter tube. The dual-lumen catheter tube extends beyond the distal end of the first catheter tube. Therefore, it is advantageous for the dual-lumen catheter tube to be made from a less rigid material than is the first catheter tube. This provides a softer distal end, which facilitates insertion of the multilumen catheter without the need for a dilator, and decreases patient discomfort.

The single lumen defined in the space between the first catheter tube and the dual-lumen catheter tube extends from the proximal end of the first catheter tube to at least one distal terminus defining at least one side opening in the first catheter tube in the vicinity of the distal end of the first catheter tube.

Each of the first and second lumens of the dual-lumen catheter tube extends through the dual-lumen catheter tube from its proximal end to a distal terminus defining an opening in the dual-lumen catheter tube. The distal terminus of the first lumen is coextensive with the distal end of the dual-lumen catheter tube. The distal terminus of the second lumen is upstream from the distal terminus of the first lumen. The distal termini of both the first and second lumens are below the distal terminus of the single lumen of the first catheter tube.

The second lumen of the dual-lumen catheter tube is eliminated below its distal terminus, thereby greatly reducing the cross-section of the distal end of the second catheter tube. This makes possible the insertion of the multilumen catheter of the present invention without the need for a dilator, and decreases patient discomfort.

A protective hub encapsulates and secures the proximal ends of both the first catheter tube and the dual-lumen catheter tube. The hub also secures and encapsulates extension tubing which is separately coupled to and in communication with each of the lumens. The protective hub facilitates fluid communication between each lumens and the fluid transfer devices or pressure monitoring devices via the extension tubing.

DESCRIPTION OF THE DRAWINGS

The invention will be more fully understood from the following solely exemplary detailed description taken in conjunction with the accompanying drawings in which:

FIG. 1A is an elevation view, partly in section, of one embodiment of the multilumen catheter of the present invention;

FIG. 1B is an enlarged perspective view of the distal portion of the multilumen catheter shown in FIG. 1A showing the distal termini and multiple lumens;

FIG. 1C is a sectional view of FIG. 1B taken along lines 1C—1C;

FIG. 3A is an enlarged, perspective view similar to that of FIG. 1B but showing a modified form of the invention;

FIG. 3B is a sectional view of FIG. 3A taken through lines 3B—3B; and

FIG. 4 is an enlarged sectional view of the proximal portion of the present invention shown in FIG. 1A.

DETAILED DESCRIPTION OF THE INVENTION

Figure 1D:
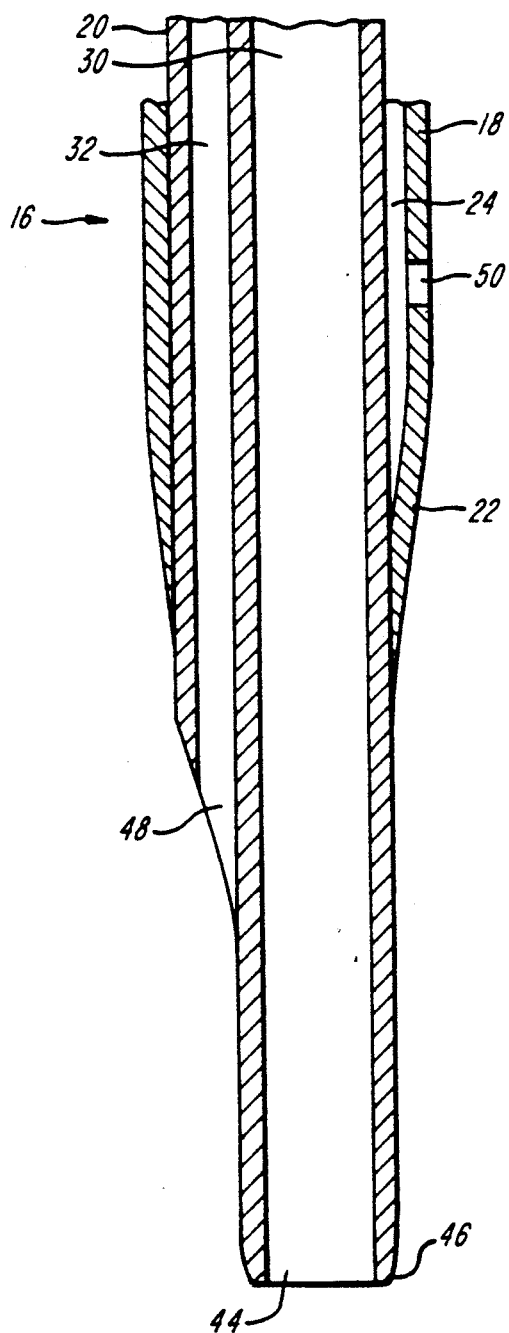
FIG. 1D is a sectional view of FIG. 1C taken along the lines 1D—1D.

Referring now to the drawings, one embodiment of the multilumen catheter according to the present invention is shown in FIGS. 1A-1D. Referring to FIG. 1A the multilumen catheter 10 comprises a flexible, elongated catheter body 12 having a proximal portion 14 and a distal portion 16. The proximal portion 14 terminates in a hub 40 which secures the catheter body 12 and facilitates fluid communication between the multilumen catheter 10 and fluid transfer devices or pressure monitoring devices via extension tubing 34, 36, 38. The distal portion 16 includes distal termini 44, 48, 50 which allow fluids entering the multilumen catheter 10 via extension tubing 34, 36, 38 to exit from the multilumen catheter 10.

The flexible elongated catheter body 12 includes a first, flexible, elongated catheter tube 18 and a flexible, elongated, dual-lumen catheter tube 20 disposed within the first catheter tube 18 and abutting a portion of the inner wall 26 of the first catheter tube 18 at least at the proximal end of tube 18. The dual-lumen catheter tube 20 extends beyond the distal end 22 of the first catheter tube 18.

Suitable materials from which the first 18 and dual-lumen 20 catheter tubes may be made include polyurethane, silicone, nylon and polyvinyl chloride (PVC), polyurethane being preferred. The dual-lumen catheter tube 20 may be made from a less rigid polyurethane than the first catheter tube 18 thereby providing a softer distal portion 16 of the multilumen catheter 10. As discussed above, a softer distal portion 16 of the multilumen catheter 10 is less traumatic for the patient.

The outer diameter of the dual-lumen catheter tube 20 is smaller than that of the first catheter tube 18. Therefore, an independent, single lumen 24 is defined in the space between the inner wall 26 of the first catheter tube 18 and the outer wall 28 of the dual-lumen catheter tube 20. The single lumen 24 extends throughout the length of the first catheter tube 18.

The dual-lumen catheter tube 20 includes first 30 and second 32 lumens integrally formed such as by extrusion and extending throughout the length of the dual-lumen catheter tube 20. For purposes of illustration, lumen 30 may have an internal diameter of 0.047 inch, which is equivalent to a 16 gauge catheter, while lumens 24 and 32 may each have an effective cross-sectional area of 0.033 inch, which is equivalent to an 18 gauge catheter.

The distal portion 16 of the multilumen catheter 10 is clearly shown in FIGS. 1B-1D. The first lumen 30 of the dual-lumen catheter tube 20 includes a distal terminus 44 which is coextensive with the distal end 46 of the dual-lumen catheter tube 20 and defines an opening in the dual-lumen catheter tube 20. The second lumen 32 includes a distal terminus 48 which is upstream from the distal terminus 44 of the first lumen 30 and defines an opening on the dual-lumen catheter tube 20. The second lumen 32 is eliminated below its' distal terminus 48 thereby reducing the cross-section of the dual-lumen catheter tube 20 at its distal end 46.

The single lumen 24 of the first catheter tube 18 has a distal terminus 50 defining a side opening in the vicinity of the distal end 22 of the first catheter tube 18. The distal terminus 50 of the single lumen 24 can be clearly seen in cross-section in FIG. 1C. The distal terminus 50 in the side of the first catheter tube 18 allows the single lumen 24 to be used to aspirate fluid from the patient as well as deliver fluid to the patient.

Furthermore, the distal end 22 of the first catheter tube 18 is tapered below the distal terminus 50 of the single lumen 24 as can be clearly seen in FIG. 1D. The tapered distal end 22 of the first catheter tube 18 in combination with the reduced cross-section of the distal end 46 of the dual-lumen catheter tube 20, makes possible the insertion of the present multilumen catheter without the need for a dilator. This would significantly reduce insertion time which is particularly desirable in emergency situations, eliminates extensive bleeding associated with the use of a dilator, and minimizes patient discomfort.

Figure 2:
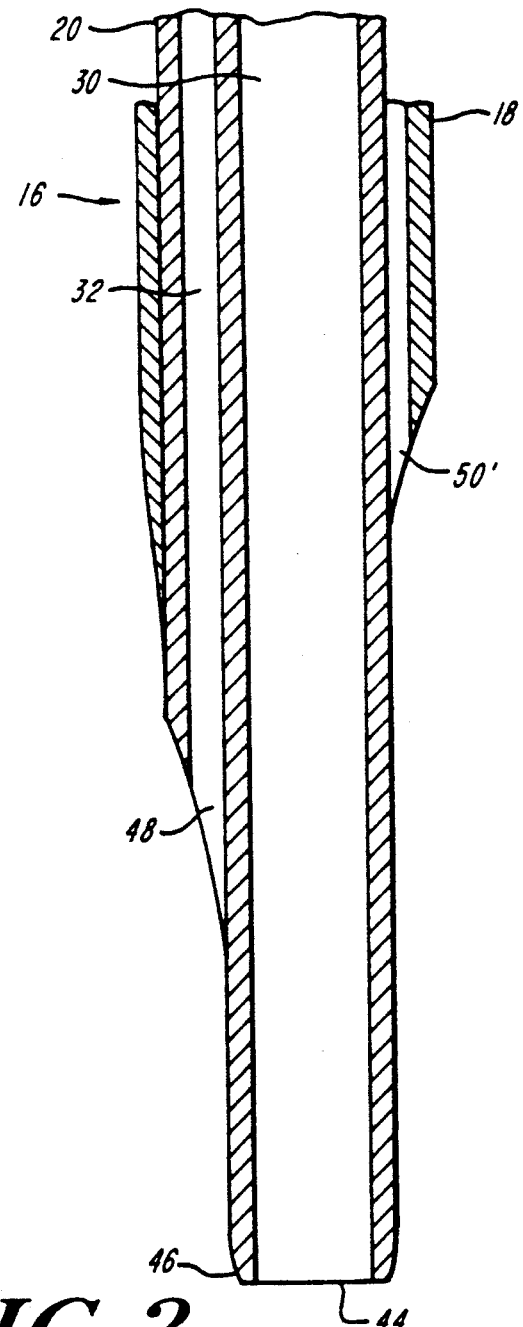
FIG. 2 is a sectional view similar to that of FIG. 1D but showing a modified form of the distal portion of the present invention.

A modification of the distal portion 16 of FIG. 1D is shown in FIG. 2. The distal terminus 50' of the single lumen 24 of the first catheter tube 18 terminates coextensively with the distal end 22 of the first catheter tube. In this configuration, the single lumen 24 may be used only to deliver fluids to the bloodstream.

Another modification of the distal portion 16 is shown in FIG. 3A. In this modification, the second lumen 32 of the dual-lumen catheter tube 20 has a distal terminus 60 defining a side opening in the dual-lumen catheter tube 20. The distal terminus 60 is upstream from the distal terminus 44 at the distal end of the dual-lumen catheter tube 20 and downstream from distal terminus 50' of the first catheter tube 18. The distal terminus 60 of the second lumen 32 is clearly shown in cross-section in FIG. 3B. The distal terminus 60 of the second lumen 32 in the side of the dual-lumen catheter tube 20 allows the second lumen 32 to be used both to aspirate fluids from and deliver fluids to the patient.

It should be understood that other configurations are possible for the distal portion 16. However, it is typical that the distal terminus 44 of the first lumen 30 is usually coextensive with the distal end 46 of the dual-lumen catheter tube 20. This allows the first lumen 30 to be used to monitor blood pressure, and to receive a guide wire necessary for insertion of the multilumen catheter of the present invention.

The proximal portion 14 of the multilumen catheter shown in FIG. 1A is clearly shown in cross-section in FIG. 4. The proximal portion 14 includes a protective hub 40 which protectively encapsulates and secures within itself the proximal end 42 of the first catheter tube 18 and the proximal end 52 of the dual-lumen catheter tube 20 which is disposed within the first catheter tube 18. It is preferable that dual-lumen catheter tube 20 extend a short distance beyond the proximal end 42 of the first catheter tube. The protective hub 40 also secures and encapsulates extension tubing 34, 36, 38 which is separately coupled to, and in communication with, each of the lumens 24, 30, 32 of the first 18 and dual-lumen 20 catheter tubes.

The protective hub 40 may be formed from suitable, sterilizable, plastic materials such as polyurethane, polycarbonate, and PVC. One technique for forming the protective hub 40 is insert molding. In this technique, rods are inserted into each of the lumens 24, 30, 32, and extension tubing of a suitable size such as 16 Ga or 18 Ga is inserted over the rods to within a short distance of the proximal ends 42, 52 of the first 18 and dual-lumen 20 catheter tubes. The proximal ends 42, 52, the rods, and the extension tubing 34, 36, 38, are placed in a mold. Molten plastic is injected into the mold. When the plastic cools, the rods are removed leaving channels 54, 56, 58 which couple extension tubing 34, 36, 38 with lumens 24, 30, 32.

Extension tubing 34, 36, 38 may be configured for coupling to fluid transfer devices, as is well known in the art. Lumens 24, 30, 32 may be opened and closed to fluid flow by way of the combination of extension tubing 24, 30, 32 and valves coupled to fluid transfer devices, as is well known in the art. A preferred valve is a Fresenius valve. However, other suitable valves are commonly used in the art.

The manner of using the multilumen catheter of the present invention is substantially the same as using a conventional multilumen catheter which is well known to those skilled in the art and need not be described in detail.

This invention is not to be limited by what has been particularly shown and described, except as indicated by the appended claims.

What is claimed is:

1. A multilumen catheter comprising:
   a first catheter tube having a proximal end, a distal end and an inner wall; and a dual-lumen catheter tube having a proximal end, a distal end, an outer wall and a cross-section which is smaller than the cross-section of said first catheter tube, said dual-lumen catheter tube disposed within said first catheter tube with at least a portion of said outer wall of said dual lumen catheter abutting at least a portion of said inner wall of said first catheter tube thereby defining a single, independent lumen in the space between the inner wall of said first catheter tube and the outer wall of said dual-lumen catheter tube, said single, independent lumen extending throughout the length of the first catheter tube and terminating with at least one distal terminus defining at least one opening in said first catheter tube, said dual-lumen catheter tube extending beyond said distal end of said first catheter tube and including first and second independent lumens integrally formed and extending throughout said dual-lumen catheter tube and each of said first and second independent lumens having a distal terminus defining an opening in said dual-lumen catheter tube, the distal terminus of said first lumen being coextensive with the distal end of said dual-lumen catheter tube, the distal terminus of said second lumen begin proximal to the distal terminus of said first lumen, and the distal terminus of each of the first and second independent lumens being distal to said distal terminus of said single, independent lumen.

2. The catheter of claim 1 further comprising:

extension tubing separately coupled to each of said first and second lumens at the proximal end of said dual-lumen catheter tube;

extension tubing separately coupled to said single lumen at said proximal end of said first catheter tube;

a protective hub encapsulating and securing the proximal end of said first catheter, tube, the proximal end of said dual-lumen catheter tube, and extension tubing coupling said single lumen, and said first and second lumens.

3. The catheter of claim 2 wherein said extension tubing is further configured for coupling to fluid transfer devices.

4. The catheter of claim 2 wherein said dual-lumen catheter tube extends beyond the proximal end of first catheter tube.

5. A multilumen catheter comprising:

a first catheter tube having a proximal end, a distal end and an inner wall; and a dual-lumen catheter tube having a proximal end, a distal end, an outer wall and a cross-section which is smaller than the cross-section of said first catheter tube, said dual-lumen catheter tube disposed within said first catheter tube and defining a single, independent lumen in the space between the inner wall of said first catheter tube and the outer wall of said dual-lumen catheter tube, said single, independent lumen extending througout the length of the first catheter tube and terminating with at least one distal terminus defining at least one opening in said first catheter tube, said dual-lumen catheter tube extending beyond said distal end of said first catheter tube and including first and second independent lumens integrally formed and extending throughout said dual-lumen catheter tube and each of said first and second independent lumens having a distal terminus defining an opening in said dual-lumen tube, the distal terminus of said first lumen being coextensive with the distal end of said dual-lumen catheter tube, the distal terminus of said second lumen being proximal to the distal terminus of said first lumen, and the distal terminus of each of the first and second independent lumens being distal to said distal terminus of said single independent lumen, said distal end of said first catheter tube being tapered distal to said distal terminus of said single independent lumen.

6. The catheter of claim 1 wherein said second lumen of said dual-lumen catheter tube is eliminated distal to said distal terminus of said second lumen.

7. A multilumen catheter comprising:

a first catheter tube having a proximal end, a distal end and an inner wall; and a dual-lumen catheter tube having a proximal end, a distal end, an outer wall and a cross-section which is smaller than the cross-section of said first catheter tube, said dual-lumen catheter tube disposed within said first catheter tube and defining a single, independent lumen in the space between the inner wall of said first catheter tube and the outer wall of said dual-lumen catheter tube, said single, independent lumen extending throughout the length of the first catheter tube and terminating with at least one distal terminus defining at least one opening in said first catheter tube, said dual-lumen catheter tube extending beyond said distal end of said first catheter tube and including first and second independent lumens integrally formed and extending throughout said dual-lumen catheter tube and each of said first and second independent lumens having a distal terminus defining an opening in said dual-lumen tube, the distal terminus of said first lumen being coextensive with the distal end of said dual-lumen catheter tube, the distal terminus of said second lumen being proximal to the distal terminus of said first lumen, and the distal terminus of each of the first and second independent lumens being distal to said distal terminus of said single independent lumen, wherein said distal terminus of said single independent lumen defines at least one side opening in said first catheter tube slightly proximal to said distal end of said first catheter tube.

8. The catheter of claim 1 wherein said distal terminus of said single lumen terminates coextensively with the distal end of said first catheter tube.

9. The catheter of claim 1 wherein said distal terminus of said second lumen defines a side opening proximal to the distal terminus of the first lumen of said dual-lumen catheter tube and distal to the distal terminus of the single lumen of the first catheter tube.

10. The catheter of claim 1 wherein said first catheter tube and said dual-lumen catheter tube are made from materials selected from the group consisting of polyurethane, silicone polyvinyl chloride (PVC), and nylon.

11. The catheter of claim 1 wherein said first catheter tube and said dual-lumen catheter are made from polyurethane.

12. A multilumen catheter comprising:

a first catheter tube having a proximal end, a distal end and an inner wall; and a dual-lumen catheter tube having a proximal end, a distal end, an outer wall and a cross-section which is smaller than the cross-section of said first catheter tube, said dual-lumen catheter tube disposed within said first catheter tube and defining a single, independent lumen in the space between the inner wall of said first catheter tube and the outer wall of said dual-lumen catheter tube, said single, independent lumen extending throughout the length of the first catheter tube and terminating with at least one distal terminus defining at least one opening in said first catheter tube, said dual-lumen catheter tube extending beyond said distal end of said first cathether tube and including first and second independent lumens integrally formed and extending throughout said dual-lumen catheter tube and each of said first and second independent lumens having a distal terminus defining an opening in said dual-lumen catheter tube, the distal terminus of said first lumen being coextensive with the distal end of said dual-lumen catheter tube, the distal terminus of said second lumen being proximal to the distal terminus of said first lumen, and the distal terminus of each of the first and second independent lumens being distal to said distal terminus of said single independent lumen, wherein said first catheter tube and said dual-lumen catheter tube are made from materials selected from the group consisting of polyurethane, silicone polyvinyl chloride (PVC), and nylon, and wherein said dual-lumen catheter tube is made from a material which is less rigid than the material from which the first catheter tube is made.

13. A multilumen catheter comprising:

a first catheter tube having a proximal end, a distal end and an inner wall; and a dual-lumen catheter tube having a proximal end, a distal end, an outer wall and a cross-section which is smaller than the cross-section of said first catheter tube, said dual-lumen catheter tube disposed within said first catheter tube and defining a single, independent lumen in the space between the inner wall of said first catheter tube and the outer wall of said dual-lumen catheter tube, said single, independent lumen extending throughout the length of the first catheter tube and terminating with at least one distal terminus defining at least one opening in said first catheter tube, said dual-lumen catheter tube extending beyond said distal end of said first catheter tube and including first and second independent lumens integrally formed and extending throughout said dual-lumen catheter tube and each of said first and second independent lumens having a distal terminus defining an opening in said dual-lumen catheter tube, the distal terminus of said first lumen being coextensive with the distal end of said dual-lumen catheter tube, the distal terminus of said second lumen being proximal to the distal terminus of said first lumen, and the distal terminus of each of the first and second independent lumens being distal to said distal terminus of said single independent lumen, wherein said first catheter tube and said dual-lumen catheter tube are made from polyurethane, and wherein said dual-lumen catheter tube is made from a less rigid polyurethane than is the first catheter tube.

* * * * *